United States Patent [19]

Conrad et al.

[11] Patent Number: 5,650,429
[45] Date of Patent: Jul. 22, 1997

[54] USE OF DL-(+/−)-α-LIPOIC ACID, D-(+)-α-LIPOIC ACID, α-LIPOIC ACID IN REDUCED OR OXIDIZED FORM OR SALTS FOR TREATING CIRCULATORY DISORDERS

[75] Inventors: Frank Conrad, Frankfurt; Hermann-August Henrich, Wurzburg; Wolfgang Geise, Dipbach; Heinz Ulrich, Niedernberg, all of Germany

[73] Assignee: Asta Medica Aktiengesellschaft, Dresden, Germany

[21] Appl. No.: 554,418

[22] Filed: Nov. 8, 1995

[30] Foreign Application Priority Data

Nov. 8, 1994 [DE] Germany ............... 44 39 477.2

[51] Int. Cl.⁶ ....................................... A61K 31/385
[52] U.S. Cl. ....................................... 514/440
[58] Field of Search ............................... 514/440

[56] References Cited

U.S. PATENT DOCUMENTS 5,318,987   6/1994   Weithmann et al. ............ 514/457

OTHER PUBLICATIONS

The Merck Index, 11th edition, p. 1469, cit#9255 1989.

WPI Abstract of Canadian Patent 2133861 (Koel Tringer) Apr. 1995.

*Primary Examiner*—Raymond Henley, III
*Attorney, Agent, or Firm*—Cushman Darby & Cushman IP Group of Pillsbury Madison & Sutro LLP

[57] ABSTRACT

The invention relates to the use of DL-(+/−)-α lipoic acid, D-(+)-α-lipoic acid, L-(−)-α-lipoic acid in reduced or oxidized form or of the metabolites and salts, esters, amides thereof for the preparation of medicines for the treatment of disorders caused by changes or disturbances in the rheological properties of the blood such as blood viscosity, erythrocyte flexibility and the aggregation of erythrocytes, in particular for the treatment of microangiopathy with disturbed microcirculation. It can also be used in the treatment of diabetics and of dialysis patients for protection of the erythrocytes, in central and peripheral circulatory disturbances and in tinnitus and hearing loss.

8 Claims, No Drawings

USE OF DL-(+/−)-α-LIPOIC ACID, D-(+)-α-LIPOIC ACID, α-LIPOIC ACID IN REDUCED OR OXIDIZED FORM OR SALTS FOR TREATING CIRCULATORY DISORDERS

BACKGROUND OF THE INVENTION

1. Field of the Invention

In circulatory disturbances therapy using rheologically active substances is gaining in importance, especially when a retrogression of rheological blockages is no longer possible. Rheologically active substances improve the blood flow. If the rheological component predominates as compared with other effects on the circulatory system, these substances which stimulate the circulation are referred to as "rheologica" (Radke et al., 1983). An increased flow capacity increases the flow of blood through the flow paths (microcirculation) and thereby also the oxygen supply to the tissues. This is particularly the case when the blood vessels can no longer continue to be supplied at the pathological initiation site and therefore the vasomotor reserve is exhausted.

2. Background Information

α-lipoic acid is referred to chemically as 1,2-dithiolane-3-pentanoic acid, 5-(1,2-dithiolane-3-yl)-valeric acid or 5-3-(1,2-dithioanyl)pentanoic acid. α-lipoic acid possesses a chiral C atom, occurs in two enantiomeric forms and is found physiologically in plants, in bacteria and in the mammalian organism. It has the function of a coenzyme in mitochondrial multienzyme complexes such as, for example, those of pyruvate dehydrogenase, of α-ketoglutarate dehydrogenase and of the dehydrogenase of the branched-chain amino acids. During metabolism α-lipoic acid can be converted from the oxidized form (disulphide bridge) to the reduced dihydro form having two free —SH groups. Both forms have a distinct antioxidizing action (for example, Kuklinski et al., 1991; Packer, 1993). The redox pair dihydrolipoic acid/α-lipoic acid moreover has metal-chelating properties. In the Federal Republic of Germany α-lipoic acid has been in use since 1966 as a medicine for the treatment of diseases of the liver, in fungal poisoning and in peripheral polyneuropathies. From knowledge of this antioxidizing action, general reference is made in DE-OS 41 38 040 A1 to a compound which catches free radicals and possesses thiol functions. The claim relates to solutions for the perfusion, conservation and reperfusion of organs and does not relate to the present invention, because here a new action in a new application has been found over and above the known antioxidizing property.

The SU Patent 1 769 865 A1 relates to the use of compounds including α-lipoic acid for the phenomenological improvement of the blood circulation and, more precisely, to the enlargement of the blood stream through the large vessels of the uterus and to the decrease of the volumetric variables in the region of the chorion in placental insufficiency.

A compound preparation containing Ginkgo biloba extract is also described in EP-OS 0 326 034 for the prophylaxis and treatment of circulatory disturbances (K öltringer, 1989).

SUMMARY OF THE INVENTION

Description of the Initial Medical Problems

1. Haemorheological disturbances lead, for example, in diabetics to a deterioration in the microcirculation and to complications associated with the diabetes. The prevalence of microaneurisms in the capillaries of the nail wall increased significantly in Type 1 diabetics, with and without retinal changes (Zaugg-Vesti et al., 1994).

2. Damage to cells is also known during haemodialysis and the quality of the dialysis is impaired.

3. Cerebral ischaemia Cerebral circulatory disturbances: in disorders of the central nervous system These are divided into 4 degrees of severity:

Stage 1: stenoses or occlusions without clinical symptoms, owing to good collateralisation via A. vertebralis and the Circulus Willisii Stage IIa: is the TIA (transitory ischaemic attack) with restituo ad integrum within 24 hours (more often paresis, more seldom paraesthesia, Amaurosis fugax, aphasia)

Stage IIb: there is residual deficit; one speaks then of PRIND (prolonged reversible ischaemic-neurological deficit)

Stage III: ischaemic insult with reversible symptoms within 4 weeks

Stage IV: permanent damage beyond 4 weeks, also referred to as IRINS (irreversible ischaemic neurological symptoms).

4. Peripheral occlusal disorder This is characterised by a disturbance of the blood flow and of the tissue perfusion.

5. There is a necessity for donor blood prophylactically in order to maintain or to improve the physiological properties of the erythrocytes.

The object was therefore to provide an effective therapy for the symptoms appearing as a result of disturbed rheological properties of the blood, namely viscosity of the blood plasma, viscosity of corpuscular constituents, flexibility, adhesiveness, ability of solid constituents, primarily of the erythrocytes and thrombocytes, to aggregate.

This object was fulfilled according to the invention by improving the blood flow through improvement of the blood viscosity, with an increase in the erythrocyte flexibility and an improvement in the pathologically altered aggregation of erythrocytes in the above-mentioned symptoms, by the administration of DL-(+/−)-α lipoic acid, D-(+)-α-lipoic acid, L-(−)-α-lipoic acid in reduced or oxidized form or of the metabolites and salts, esters, amides thereof, in the form of medicaments for the prevention and treatment of disorders caused by changes or disturbances in the rheological properties of the blood, such as blood viscosity, erythrocyte flexibility and the aggregation of erythrocytes.

The invention therefore primarily provides the use for the preparation of medicaments containing DL-(+/−)-α lipoic acid, D-(+)-α-lipoic acid, L-(−)-α-lipoic acid in reduced or oxidized form or of the metabolites and salts, esters, amides thereof for the prevention and treatment of: disturbed microcirculation in microangiopathy, protection of the erythrocytes in dialysis patients, cerebral and peripheral arterial circulatory disturbances, for administration prior to blood donation, in tinnitus and hearing loss. In addition there is the further possibility of use in the case of patients with cardiac operations who require a heart-lung machine, patients with cardiac defects, patients with valvular prostheses and additionally in the field of angiological operations (such as balloon dilatation) prior to cardiac operations and heart transplants.

DETAILED DESCRIPTION OF THE INVENTION

Method

The specific method of sinusoidal oscillating capillary rheometry (Chmiel H., 1990) was used to prove the activity of α-lipoic acid and/or of its enantiomers, and/or of its derivatives. The viscoelastic flow behaviour of blood is used in clinical haemorheology as the most up-to-date method for determining pathological alterations in the erythrocytes (for example, in arterial occlusal disorder, apoplectic stroke and generally in disorders of the peripheral vessels).

To determine the viscoelasticity, dynamically rheological experiments are carried out wherein the deformation and the shear stress are measured at given time intervals (sinusoidal oscillating shear tests). As a non-linear viscoelastic liquid, blood shows a decrease of $\eta'$ and $\eta''$ with increasing amplitude of shear. The measurements carried out here under "Examples" were made using the Oscillating Capillary Rheometer OCR-D (A. Paar, Graz, Austria), with the method being based on a simultaneous determination of the volumetric flow rate and of the pressure gradient along a circular glass capillary. The viscoelasticity can vary in manner between elastic deformations (storage of energy) and viscous deformations (energy consumption). Increasing values of $\eta''$ denote increasingly more elastic erythrocytes (less flexible) with formation of aggregates, which lead to disturbances of the blood flow in the microcirculation. These properties are associated with the structure of the cell membrane and with the "bridging" mechanisms, which lead to the above-mentioned rouleaux formation. The decrease of $\eta'$ at higher shear rates can be due to altered orientations and extension of the erythrocytes as well as to a reduction in the energy consumption. $\eta'$ is dependent not only on the haematocrit and the plasma viscosity but also on the aggregation behaviour and the elastic property of the membrane. The invention is demonstrated by means of the following experiments.

1.) EX vivo- in vitro investigations

Using human blood and the erythroconcentrates thereof, experiments on viscoelasticity were carried out by Herr Prof. Dr. Henrich at the Würzburg University Clinic.

The blood, to which α-lipoic acid had been added, was maintained under storage conditions for given time intervals. At the different measuring points the blood was resuspended in the autologous plasma and to it was added phenazine methosulphate (PMS), which simulates the ischaemic situation in the patient (method; Maridonneau et al. 1983; Maridonneau-Parini and Harpey, 1985).

The dynamic component of the blood viscosity, $\eta'$

For example, when the two enantiomers of α-lipoic acid are used, there results a distinct, in most cases highly significant decrease in the blood viscosity as compared with the control. The relative difference is 10%.

The elastic component of the blood viscosity, $\eta''$

Here the relative difference as compared with the control is a 20% improvement.

2.) Experimental investigations on animals

In experimental diabetes in rats an improvement in the perineural blood flow was measured by Prof. Dr. Low, Mayo Clinic, Rochester, USA. The blood circulation through the peripheral nervous system of the diabetic rats was increased by means of thioctic acid by 50% as compared with the control (untreated diabetic animals) ($p<0.001$).

3.) Investigations on the nail wall

Seven patients having diabetic polyneuropathy were treated for 6 weeks with thioctic acid 2×600. At the beginning and at the end of the period an investigation on the nail wall was carried out by means of a capillary microscope. Within the framework of the investigation a function test was carried out, a 3-minute ischaemia with subsequent reperfusion. The target variable was the time taken to achieve the reperfusion rate. Prior to treatment the time was 76.8±25.2 sec and after 6 weeks of treatment was 21.4±8.1 sec.

The preparation of the salt was carried out in a known manner (see also Patent Specification EP-A 427 247, incorporated herein by reference). The pharmaceutical preparations in general contain from 5 mg to 3 g as a single dose of the compounds used according to the invention. The active level obtained in the body after repeated dosage should preferably be between 0.1 and 100 mg/kg of body weight. The administration takes place in the form of tablets, capsules, granules, chewing tablets, sucking tablets, pills, dragees, effervescent tablets, effervescent powders, solutions ready for drinking, liquid forms for parenteral application. Solutions ready for drinking and liquid forms for parenteral application may be alcoholic and aqueous solutions, suspensions and emulsions.

Examples of preferred forms of application are tablets containing preferably between 5 mg and 2 g of the compounds used according to the invention and solutions containing preferably between 1 mg and 200 mg of the compounds used according to the invention per ml of liquid.

Examples of single doses of the active substance are:

a. oral forms: 10 mg to 3 g b. parenteral forms (intravenous or intramuscular): 10 mg to 12 g The doses a) and b) can be given, for example, 1 to 6 times daily or as a continuous infusion.

Examples of pharmaceutical use

EXAMPLE 1

Tablets containing 100 mg of D-(+)-α-lipoic acid 250 g of D-(+)-α-lipoic acid is evenly triturated together with 750 g of microcrystalline cellulose. After the mixture has been sieved, 250 g of starch (starch 1500/Colorcon), 732.5 g of lactose, 15 g of magnesium stearate and 2.5 g of highly-disperse silica are admixed and the mixture is pressed to form tablets having a weight of 800.00 mg.

One tablet contains 100 mg of D-(+)-α-lipoic acid. Optionally the tablets can be provided with a film coating which is soluble in or permeable by gastric juices.

EXAMPLE 2

Ampoules containing 250 mg of D-(+)-α-lipoic acid as trometamol salt in 10 ml 250 g of D-(+)-α-lipoic acid together with 352.3 g of trometamol (2-amino-2-(hydroxymethyl)-1,3-propanediol) are dissolved with stirring in a mixture of 9 liters of water for injection purposes and 200 g of 1,2-propylene glycol. The solution is made up to a volume of 10 liters with water for injection purposes and subsequently filtered through a membrane filter of a pore size of 0.2 μm and having a glass-fibre prefilter. The filtrate is drawn off under aseptic conditions in 10 ml portions into sterilised 10 ml ampoules.

One ampoule contains 250 mg of D-(+)-α-lipoic acid as trometamol salt in 10 ml of injection solution.

EXAMPLE 3

Ampoules containing 250 mg of D-(+)-α-dihydrolipoic acid in 10 ml of injection solution 60 mg of trometamol and 1 g of ethylenediaminetetraacetic acid, disodium salt, are dissolved in 1.8 liters of water for injection purposes. The solution is gassed with nitrogen for a period of 30 minutes. Under continued gassing with nitrogen, 2 g of sodium disulphite and subsequently 50 g of D-(+)-α-dihydrolipoic acid are dissolved in the mixture. The solution is made up to a volume of 2 liters using water for injection purposes which has been gassed with nitrogen.

After being carefully mixed, the solution is filtered through a membrane filter of a pore size of 0.2 µm and the filtrate is drawn off, under aseptic conditions and with previous and subsequent gassing with nitrogen, into ampoules to a filling volume of 10 ml.

One ampoule contains 250 mg of D-(+)-α-dihydrolipoic acid as trometamol salt in 10 ml of solution.

Citations to references contained herein are listed below for convenience and are hereby incorporated by reference.

Chmiel, H. et al. (1990) Biorheology 27:883–94.

Maridonneau et al. (1983) Biochim. Biophys. Acta 42:S58–62.

Maridonneau et al. (1983) J. Biol. Chem. 258:3107–13.

Maridonneau-Parini and Harpey (1985) Br. J. Clin. Pharmacol. 20:148–51.

What is claimed is:

1. A method for treating disorders or rheological syndromes caused by changes or disturbances in blood viscosity, erythrocyte flexibility or the aggregation of erythrocytes, said method comprising administering an effective amount of DL-(+/−)-α lipoic acid, D-(+)-α-lipoic acid, and/or L-(−)-α-lipoic acid in reduced or oxidized form or a tromethamol salt thereof.

2. The method of claim 1 wherein said disorder is disturbed microcirculation in microangiopathy.

3. A method for protecting erythrocytes and improving blood circulation in dialysis patients comprising administering an effective amount of DL-(+/−)-α lipoic acid, D-(+)-α-lipoic acid, and/or L-(−)-α-lipoic acid in reduced or oxidized form, or a tromethamol salt thereof.

4. A method of treating peripheral arterial circulatory disturbances comprising administering an effective amount of DL-(+/−)-α lipoic acid, D-(+)-α-lipoic acid, and/or L-(−)-α-lipoic acid in reduced or oxidized form or a tromethamol salt thereof.

5. The method of claim 4 wherein the peripheral arterial circulatory disturbance is in stage II, stage IIa or stage IIb according to Fontaine.

6. A method for improving the quality of donor blood comprising administering to a blood donor prior to blood donation DL-(+/−)-α lipoic acid, D-(+)-α-lipoic acid, and/or L-(−)-α-lipoic acid in reduced or oxidized form or a tromethamol salt thereof.

7. A method for improving microcirculatory circulation of the brain in patients with dementia caused by age or infarction comprising administering an effective amount of DL-(+/−)-α lipoic acid, D-(+)-α-lipoic acid, and/or L-(−)-α-lipoic acid in reduced or oxidized form or a tromethamol salt thereof.

8. A method for treating tinnitus or hearing loss comprising administering an effective amount of DL-(+/−)-α lipoic acid, D-(+)-α-lipoic acid, and/or L-(−)-α-lipoic acid in reduced or oxidized form or of the metabolites and salts, esters, amides thereof.

* * * * *